(12) United States Patent
Li et al.

(10) Patent No.: US 11,240,997 B2
(45) Date of Patent: Feb. 8, 2022

(54) METHOD FOR PREPARING PORCINE FIBROBLASTS WITH BOTH CD163 GENE AND CD13 GENE BEING KNOCKED-OUT

(71) Applicant: Shandong Landsee Genetics Co., Ltd., Rizhao (CN)

(72) Inventors: Kui Li, Beijing (CN); Yulian Mu, Beijing (CN); Zhiguo Liu, Beijing (CN); Julang Li, Guelph (CA); Kui Xu, Beijing (CN); Yinghui Wei, Beijing (CN); Changli Ge, Rizhao (CN); Xuehui Cai, Harbin (CN); Long Wang, Rizhao (CN); Qimei Chen, Rizhao (CN); Yang Qiu, Rizhao (CN)

(73) Assignee: Shandong Landsee Genetics Co., Ltd., Rizhao (CN)

( * ) Notice: Subject to any disclaimer, the term of this patent is extended or adjusted under 35 U.S.C. 154(b) by 100 days.

(21) Appl. No.: 16/379,638

(22) Filed: Apr. 9, 2019

(65) Prior Publication Data
US 2020/0323182 A1   Oct. 15, 2020

(51) Int. Cl.
| C12N 15/00 | (2006.01) |
| A01K 67/027 | (2006.01) |
| C12N 9/22 | (2006.01) |
| C12N 5/077 | (2010.01) |
| C12Q 1/6881 | (2018.01) |
| C12N 15/11 | (2006.01) |
| C12N 15/85 | (2006.01) |
| C12N 15/877 | (2010.01) |
| C12N 5/16 | (2006.01) |
| C12N 15/64 | (2006.01) |
| C12N 15/79 | (2006.01) |
| C12N 15/113 | (2010.01) |

(52) U.S. Cl.
CPC ...... *A01K 67/0276* (2013.01); *A01K 67/0273* (2013.01); *C12N 5/0652* (2013.01); *C12N 5/16* (2013.01); *C12N 9/22* (2013.01); *C12N 15/11* (2013.01); *C12N 15/1138* (2013.01); *C12N 15/64* (2013.01); *C12N 15/79* (2013.01); *C12N 15/8509* (2013.01); *C12N 15/8778* (2013.01); *C12Q 1/6881* (2013.01); *A01K 2217/075* (2013.01); *A01K 2227/108* (2013.01); *C12N 2310/20* (2017.05); *C12N 2510/00* (2013.01); *C12N 2517/04* (2013.01)

(58) Field of Classification Search
USPC ........................................... 435/230.1; 800/8
See application file for complete search history.

(56) References Cited

U.S. PATENT DOCUMENTS

2020/0045945 A1\* 2/2020 Lillico ................. C12N 15/102

FOREIGN PATENT DOCUMENTS

| CN | 107354170 | \* 11/2017 |
| CN | 107893088 | \* 4/2018 |
| CN | 108753832 | \* 11/2018 |
| CN | 108823248 | \* 11/2018 |

OTHER PUBLICATIONS

Whitworth (Biol, Reprod., 2014, vol. 91, No. 3, p. 1-13).\*
Whitworth (Nature Biotech., Jan. 2016, Published online Dec. 7, 2015, vol. 34, No. 1, p. 20-22).\*
Wells (J. Virol., 2017, vol. 91, No. 2, e01521-16, p. 1-11).\*
Yang (Antiviral Res., 2018, vol. 151, p. 63-70).\*
Burkard (J. Virol., 2018, vol. 92, No. 16, e00415-18, p. 1-14).\*
Translation of CN107893088, 2018.\*
Translation of CN108823248, 2018.\*
Translation of CN108753832, 2018.\*
Translation of CN107354170, 2017.\*
Cong (Science, 2013, vol. 339, p. 819-823).\*

\* cited by examiner

*Primary Examiner* — Michael C Wilson
(74) *Attorney, Agent, or Firm* — Hogan Lovells US LLP

(57) ABSTRACT

Provided is a double-gene knockout vector system, a method for preparing porcine fibroblasts with both CD163 gene and CD13 gene being knocked-out, prepared porcine fibroblasts, and a method for preparing a gene-edited pig with both CD163 gene and CD13 gene being knocked-out. The vector system of the present disclosure comprises a CD163 gene knockout vector and a CD13 gene knockout vector. The CD163 gene knockout vector comprises a gene editing vector backbone and a DNA fragment ligated to the gene editing vector backbone, with a nucleotide sequence of the DNA fragment being shown in any one of SEQ ID NOs: 1-3. The CD13 gene knockout vector comprises a gene editing vector backbone and a DNA fragment ligated to the gene editing vector backbone, a nucleotide sequence of the DNA fragment being shown in any one of SEQ ID NOs: 4-6.

8 Claims, 1 Drawing Sheet
Specification includes a Sequence Listing.

```
pAPN
WT:        TCGGCGTGGCGGCCGTGGCC

CD13-125:  TCGGC--------CGTGGCC  -8bp

CD13-132:  TCGGC---------GTGGCC  -9bp

CD163
WT:        AAACCCAGGCTGGTTGGAGGGGACATTCCCTGC

CD163-125: AAACCCAGGCTGG--------GACATTCCCTGC  -8bp
           AAACCCAGGCTGGTTGGAGGGGACATTCCCTGC

CD163-132: AAACCCAGG-TGGTTGGAGGGGACATTCCCTGC  -1bp
           AAACCCAGGCTGGTTGGAGGGGACATTCCCTGC
```

METHOD FOR PREPARING PORCINE FIBROBLASTS WITH BOTH CD163 GENE AND CD13 GENE BEING KNOCKED-OUT

SEQUENCE LISTING

This application contains a sequence listing, which was filed herewith and is incorporated by reference in its entirety. The sequence listing is an ASCII text file named: 046231_0000025_Sequence_Listing, created Apr. 9, 2019 and is 4.20 KB.

TECHNICAL FIELD

The present disclosure relates to the field of gene editing, and in particular to a method for preparing porcine fibroblasts with both CD163 gene and CD13 gene being knocked-out.

BACKGROUND

Porcine reproductive and respiratory syndrome (PRRS) is a highly contagious disease caused by porcine reproductive and respiratory syndrome virus (PRRSV), which is characterized by reproductive disorders and respiratory diseases and high mortality in piglets and growing pigs, such as porcine anorexia, fever, premature delivery of pregnant sows, late abortion, stillbirth, weak fetus and mummified fetus. As the disease is clinically manifested as ear cyanosis, it is also known as "blue ear disease". The disease was first discovered in the United States in 1987, followed by the outbreak in Europe in 1989. The first outbreak in mainland China at the end of 1995. The infection rate of the disease in pigs was as high as 90%, which brought great economic losses to the pig industry. It has become an infectious disease that seriously harms the pig industry worldwide.

PRRSV mainly infects well-differentiated porcine alveolar macrophages (PAM) in vivo. Prerequisite for PRRSV to infect target cells is adsorption with host cells, and receptors on the surface of host cells are essential to achieve this adsorption. It is found that heparin sulfate (HS), sialoadhesin (Sn) and CD163 (Cluster of Differentiation 163) molecules are three important receptor molecules present on PAM that can bind to PRRSV. Among them, CD163 is a cysteine-rich scavenger receptor, is a typical type I glycosylated protein, and is also an antigen for macrophage differentiation. Its molecular weight is 130 kD, so it is also called M130 protein. CD163 was originally recognized as a protein for specific recognition of macrophages and monocytes, which is expressed in macrophages of lung, spleen, liver, lymph node, and thymus tissue. Some studies have shown that expression of CD163 molecules on PRRSV non-susceptible cell lines (BHK-21 and PK-15) via transfection can allow these cell lines to be infected with PRRSV and to produce progeny virions in the cells. Anti-human CD163 antibodies can block infection with PRRSV, indicating that CD163 is an essential receptor for PRRSV infection. Domain SRCR5 of CD163 protein is essential for viral infection of cells, while four SRCRs at the amino terminus and the cytoplasmic tail are not essential, wherein the SRCR5 domain is encoded by exon 7 of CD163. Therefore, studies on CD163 gene-modified pigs can provide the necessary evidence for whether CD163 receptor plays an important role in PRRSV infection.

Porcine epidemic diarrhea (PED) is a highly contagious intestinal disease caused by porcine epidemic diarrhea virus (PEDV). Pigs of any age, especially piglets, can be infected, with a mortality rate being very high. Specially, for newborn piglets within 7 days of age, the mortality rate can be as high as 100% in the absence of effective maternal antibodies. For adult pregnant sows, the reproductive performance after infection is affected, leading to for example, miscarriage of the sows in the early pregnancy and decreased conception rate after infection. Fattening pigs will lose weight after PEDV infection.

Recent studies have shown that PEDV primarily infects piglets by binding to CD13 (APN) of epithelial cells of porcine small intestine mucosa. CD13 is of great significance as a necessary binding receptor for PEDV invading cells, providing a new idea for the breeding of new varieties of pigs against epidemic diarrhea virus, which is to prevent PEDV infection in pigs by knocking out APN gene of pigs.

Therefore, establishing a method for rapidly, accurately and effectively knocking out CD163 gene and CD13 gene in pigs simultaneously to obtain porcine fibroblasts or pigs with CD163 gene and CD13 gene being knocked-out is of great significance in studying pig blue ear disease and porcine epidemic diarrhea and the breeding of disease-resistant pigs.

SUMMARY OF THE INVENTION

The present disclosure provides a double-gene knockout vector system, wherein the double-gene knockout vector system comprises a CD163 gene knockout vector and a CD13 gene knockout vector, wherein:

the CD163 gene knockout vector comprises a first gene editing vector backbone and a first DNA fragment ligated to the first gene editing vector backbone, with a nucleotide sequence of the first DNA fragment being shown in any one of SEQ ID NOs: 1-3; and the CD13 gene knockout vector comprises a second gene editing vector backbone and a second DNA fragment ligated to the second gene editing vector backbone, with a nucleotide sequence of the second DNA fragment being shown in any one of SEQ ID NOs: 4-6.

The present disclosure provides a method for preparing porcine fibroblasts with both CD163 gene and CD13 gene being knocked-out, wherein the method comprises:

(1) providing a double-gene knockout vector system of the present disclosure; and (2) introducing the double-gene knockout vector system into porcine fibroblasts.

The present disclosure provides porcine fibroblasts with both CD163 gene and CD13 gene being knocked-out prepared by the method for preparing porcine fibroblasts with both CD163 gene and CD13 gene being knocked-out according to the present disclosure.

The present disclosure provides a pig with both CD163 gene and CD13 gene being knocked-out.

BRIEF DESCRIPTION OF DRAWINGS

In order to more clearly illustrate the technical solutions of the detailed embodiments of the present disclosure or the prior art, brief description is made below on the drawings required to be used in the detailed embodiments or the prior art. It should be understood that the following drawings only illustrate some of the embodiments of the present disclosure and shall not be regarded as a limitation to the scope of the present disclosure. For a person skilled in the art, other drawings may be obtained according to these drawings without inventive effort.

DETAILED DESCRIPTION OF THE INVENTION

Figures 1, 2:
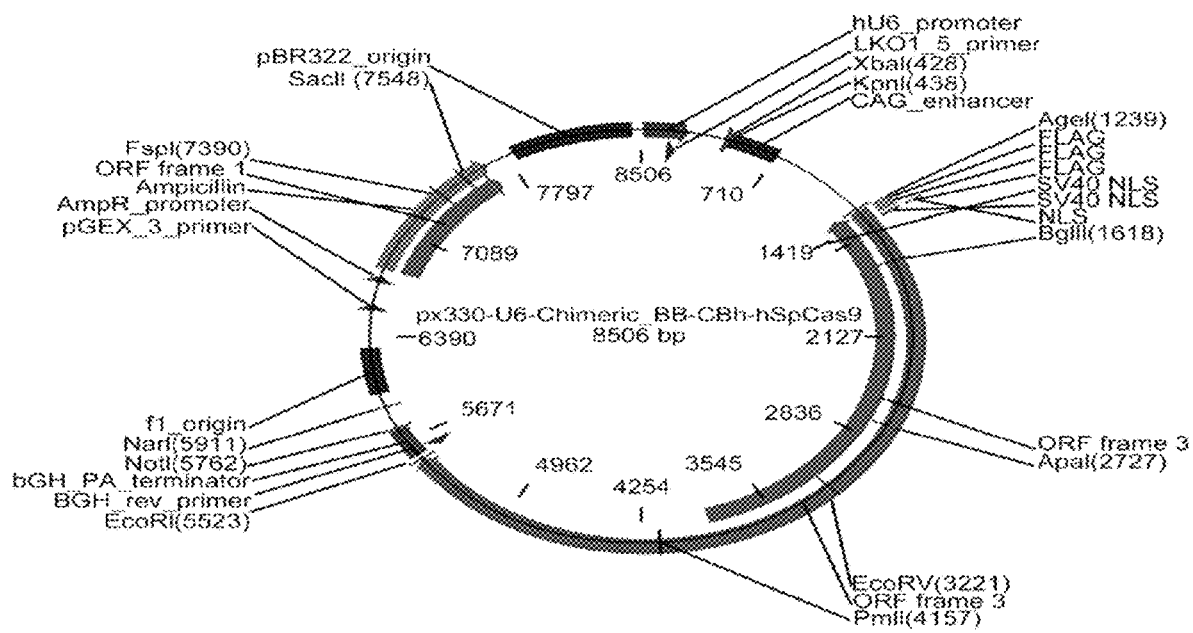
FIG. 1 is a map of pX330 vector backbone.
FIG. 2 shows genotypes of two double-gene knockout cell lines.

The technical solutions of the present disclosure will be described in detail below with reference to the embodiment.

Those skilled in the art will understand that the following embodiments are only intended to illustrate the disclosure, and should not be construed as limiting the scope of the disclosure. Examples are carried out according to the conventional conditions or the conditions recommended by the manufacturer, if specific conditions are not described. All reagents or instruments used, whose manufacturers are not indicated, are commercially available conventional products.

The objects of the present disclosure comprises, for example, providing a double-gene knockout vector system comprising a CD163 gene knockout vector and a CD13 gene knockout vector, by which easy, quick, efficient and site-directed knockout of CD163 gene and CD13 gene can be achieved.

The object of the present disclosure also comprises, for example, a method for preparing porcine fibroblasts with both CD163 gene and CD13 gene being knocked-out. By the method, porcine fibroblasts with CD163 gene and CD13 gene being homozygously knocked-out, without any exogenous marker are simply, quickly and efficiently obtained. It is of great significance for studies of blue ear disease, porcine epidemic diarrhea and breeding of disease-resistant pigs.

The object of the present disclosure also comprises, for example, providing porcine fibroblasts with both CD163 gene and CD13 gene being knocked-out, prepared by the above method. CD163 gene and CD13 gene may be knocked-out in porcine fibroblasts in a homozygous manner. It is of great significance for studies of blue ear disease, porcine epidemic diarrhea and breeding of disease-resistant pigs.

The object of the present disclosure also comprises, for example, a method for preparing a gene-edited pig with both CD163 gene and CD13 gene being knocked-out. By the method, a gene-edited pig with CD163 gene and CD13 gene being homozygously knocked-out is simply and efficiently obtained. It is of great significance for studies of blue ear disease, porcine epidemic diarrhea and breeding of disease-resistant pigs.

The present disclosure provides a double-gene knockout vector system, wherein the double-gene knockout vector system comprises a CD163 gene knockout vector and a CD13 gene knockout vector, wherein:

the CD163 gene knockout vector comprises a gene editing vector backbone and a DNA fragment ligated to the gene editing vector backbone, with a nucleotide sequence of the DNA fragment being shown in any one of SEQ ID NOs: 1-3; for example SEQ ID NO: 1; and the CD13 gene knockout vector comprises a gene editing vector backbone and a DNA fragment ligated to the gene editing vector backbone, with a nucleotide sequence of the DNA fragment being shown in any one of SEQ ID NOs: 4-6, preferably SEQ ID NO: 4.

The vector backbones of the CD163 gene knockout vector and the CD13 gene knockout vector are selected from the group consisting of CRISPR/Cas9, CRISPR/Cas9n, CRISPR/Cpf1 and CRISPR/C2c2.

Traditional gene knockout systems are based primarily on ZFN and TALEN technologies, which require complex operations and considerable effort to knock out target genes. The above-mentioned gene knockout vector of the present disclosure belongs to the CRISPR gene editing system, and the target gene is site-directed knocked-out by using the CRISPR technology, thereby greatly reducing the operation difficulty of the gene knockout and improving the knockout efficiency. Moreover, in the present disclosure, double-gene editing is achieved by one operation, without introducing exogenous marker gene, which has advantages of high efficiency, high precision, simple operation and high safety. In another aspect, the present disclosure optimizes gRNAs thereof for knockout of CD163 gene and CD13 gene, and screens the gRNA with the highest knockout efficiency from multiple gRNAs, overcoming defect of high off-target rate of a knockout process of the CRISPR gene editing system and further improving the efficiency of targeting. Thereby a homozygote with target gene CD163 gene and CD13 gene being knocked-out can be quickly obtained.

In one or more embodiments, the vector backbones of the CD163 gene knockout vector and the CD13 gene knockout vector are CRISPR/Cas9, preferably, the CRISPR/Cas9 being selected from the group consisting of pX330, pX260, pX334, pX335, pX458, pX459, pX461, pX462, pX551 and pX552, more preferably, the CRISPR/Cas9 being pX330.

The present disclosure further provides a method for preparing porcine fibroblasts with both CD163 gene and CD13 gene being knocked-out, wherein the method comprises:

(1) providing the above double-gene knockout vector system according to the present disclosure; and (2) introducing the double-gene knockout vector system into porcine fibroblasts, screening and identifying the porcine fibroblasts to obtain monoclonal cells with both CD163 gene and CD13 gene being knocked-out.

The above method of the present disclosure is established based on the aforementioned gene knockout vector, by which porcine fibroblasts with CD163 gene and CD13 gene being homozygously knocked-out, not carrying any exogenous marker can be obtained simply, rapidly and efficiently. It is of great significance for studies of porcine blue ear disease, porcine epidemic diarrhea and breeding of disease-resistant pigs.

In one or more embodiments, the porcine fibroblasts are porcine fetal fibroblasts.

In one or more embodiments, the step (1) comprises: annealing two complementary oligonucleotide single strands for CD163 to form a double strand, ligating with an enzyme-digested vector backbone, screening for a positive clone to obtain a CD163 gene knockout vector, wherein sequences of the two complementary oligonucleotide single strands for CD163 are set forth in SEQ ID NOs: 7-8, SEQ ID NOs: 9-10, or SEQ ID NOs: 11-12; and annealing two complementary oligonucleotide single strands to form a double strand, ligating with an enzyme-digested vector backbone, and screening for a positive clone to obtain a CD13 gene knockout vector, wherein sequences of the two complementary oligonucleotide single strands for CD13 are set forth in SEQ ID NOs:13-14, SEQ ID NOs: 15-16, or SEQ ID NOs: 17-18.

In one or more embodiments, in the step (2), the introduction of the CD13 gene knockout vector and the CD163 gene knockout vector into porcine fibroblasts is performed by electroporation, and the screening of the monoclonal cells is performed by limited dilution method, followed by identification of whether the monoclonal cells are positive monoclonal cells with both CD163 gene and CD13 gene being knocked-out.

In one or more embodiments, in step (2), the identification comprises: extracting genomic DNA from the monoclonal cells using primers as set forth in SEQ ID NOs: 19-20 and SEQ ID NOs: 21-22, respectively, performing PCR amplification, sequencing the amplification product, and determining whether the monoclonal cells are positive monoclonal cells with both CD163 gene and CD13 gene being knocked-out according to the sequencing result. Preferably, for a PCR amplification using SEQ ID NOs: 19-20 as primers, an annealing temperature is 60-62° C., with 32-38 cycles, more preferably 61° C., with 36 cycles. For a PCR amplification using SEQ ID NOs: 21-22 as primers, an annealing temperature is 57-59° C., with 32-36 cycles, more preferably, 58° C., with 34 cycles.

The present disclosure also provides porcine fibroblasts with CD163 gene and CD13 gene being knocked-out prepared by the above method. In the above-mentioned porcine fibroblasts of the present disclosure, both CD163 gene and CD13 gene are knocked-out, and no exogenous marker genes are introduced, which is of great significance for studies on porcine blue ear disease, porcine epidemic diarrhea and breeding of disease-resistant pigs.

The present disclosure also provides a method for preparing a gene-edited pig with both CD163 gene and CD13 gene being knocked-out, comprising transferring a cell nucleus of the above-mentioned porcine fibroblasts serving as donor cells for nuclear transfer into an enucleated oocyte, preparing a recombinant cloned embryo and transplanting to a mother body for pregnancy to obtain a gene-edited pig with both CD163 gene and CD13 gene being knocked-out. The above method of the present disclosure is based on the aforementioned porcine fibroblasts with CD163 gene and CD13 gene being knocked-out. By the method, a gene-edited pig whose CD163 gene is knocked-out and CD13 gene is knocked-out, which is of great significance for studies of porcine blue ear disease, porcine epidemic diarrhea and breeding of disease-resistant pigs.

In one or more embodiments, the method further comprises a step of identifying the gene-edited pig, wherein the step of the identification comprises extracting genomic DNA of the pig, performing amplification of the extracted genomic DNA using upstream and downstream primers with nucleotide sequences shown as SEQ ID NOs: 19-20 and SEQ ID NOs: 21-22, performing agarose gel electrophoresis or sequencing on the amplified product, and determining whether CD163 gene and CD13 gene have been knocked-out according to the electrophoresis or sequencing results. Preferably, for a PCR amplification using SEQ ID NOs: 19-20 as primers, an annealing temperature is 60-62° C., with 32-38 cycles, more preferably 61° C., with 36 cycles. For a PCR amplification using SEQ ID NOs: 21-22 as primers, an annealing temperature is 57-59° C., with 32-36 cycles, more preferably, 58° C., with 34 cycles.

In one or more embodiments, the vector backbones of the CD163 gene knockout vector and the CD13 gene knockout vector are selected from the group consisting of CRISPR/Cas9, CRISPR/Cas9n, CRISPR/Cpf1 and CRISPR/C2c2.

In one or more embodiments, a nucleotide sequence of the first DNA fragment is set forth in SEQ ID NO: 1.

In one or more embodiments, a nucleotide sequence of the second DNA fragment is set forth in SEQ ID NO:4.

In one or more embodiments, the vector backbones of the CD163 gene knockout vector and the CD13 gene knockout vector (also named the first gene editing vector backbone and the second gene editing vector backbone, respectively) are CRISPR/Cas9.

In one or more embodiments, the CRISPR/Cas9 is selected from the group consisting of pX330, pX260, pX334, pX335, pX458, pX459, pX461, pX462, pX551, and pX552.

In one or more embodiments, the CRISPR/Cas9 is pX330.

The present disclosure provides a method for preparing porcine fibroblasts with both CD163 gene and CD13 gene being knocked-out, wherein the method comprises:

(a) providing a double-gene knockout vector system of the present disclosure; and
(b) introducing the double-gene knockout vector system into porcine fibroblasts.

In one or more embodiments, the method for preparing porcine fibroblasts with both CD163 gene and CD13 gene being knocked-out further comprises:

(c) screening and identifying the porcine fibroblasts to obtain monoclonal cells with both CD163 gene and CD13 gene being knocked-out.

In one or more embodiments, the porcine fibroblasts are porcine fetal fibroblasts.

In one or more embodiments, the step (a) comprises: annealing a first pair of complementary oligonucleotide single strands to form a double strand, ligating with an enzyme-digested vector backbone, screening for a positive clone to obtain a CD163 gene knockout vector, wherein sequences of the first pair of complementary oligonucleotide single strands are set forth in SEQ ID NOs: 7-8, SEQ ID NOs: 9-10, or SEQ ID NOs: 11-12; and annealing a second pair of complementary oligonucleotide single strands to form a double strand, ligating with an enzyme-digested vector backbone, and screening for a positive clone to obtain a CD13 gene knockout vector, wherein sequences of the second pair of complementary oligonucleotide single strands are set forth in SEQ ID NOs:13-14, SEQ ID NOs: 15-16, or SEQ ID NOs: 17-18.

In one or more embodiments, in the step (b), the introduction of the CD13 gene knockout vector and the CD163 gene knockout vector into porcine fibroblasts is performed by electroporation.

In one or more embodiments, in the step (c), the screening of the monoclonal cells is performed by limited dilution method, followed by identification of whether the monoclonal cells are positive monoclonal cells with both CD163 gene and CD13 gene being knocked-out.

In one or more embodiments, in step (c), the identification comprises: extracting genomic DNA from the monoclonal cells using primers as set forth in SEQ ID NOs: 19-20 and SEQ ID NOs: 21-22, respectively, performing PCR amplification, sequencing the amplification product, and determining whether the monoclonal cells are positive monoclonal cells with both CD163 gene and CD13 gene being knocked-out according to the sequencing result.

In one or more embodiments, the method for preparing a gene-edited pig with both CD163 and CD13 being knocked-out further comprises a step of identifying the gene-edited pig, wherein the step of the identification comprises extracting genomic DNA of the pig, performing amplification of the extracted genomic DNA using upstream and downstream primers with nucleotide sequences shown as SEQ ID NOs: 19-20 and SEQ ID NOs: 21-22, performing agarose gel electrophoresis or sequencing on the amplified product, and determining whether CD163 gene and CD13 gene have been knocked-out according to the electrophoresis or sequencing results.

In one or more embodiments, the gene-edited pig with both CD163 and CD13 being knocked-out is resistant to porcine reproductive and respiratory syndrome virus and the porcine epidemic diarrhea virus. Without being limited by theory, it is believed that inhibition of CD163 expression can suppress PRRSV infection and thus resist PRRSV, while inhibition of CD13 expression can inhibit PEDV infection in pigs, thereby making pigs resistant to PEDV. In addition, pigs with both CD163 gene and CD13 gene being knocked-out can also be used for mechanistic and clinical studies on PRRSV and PEDV.

In one or more embodiments, the gene-edited pig with both CD163 and CD13 being knocked-out is the one prepared by the above-mentioned method for preparing a gene-edited pig with both CD163 and CD13 being knocked-out.

The present disclosure constructs a vector system for knocking out CD163 gene and CD13 gene, by using a CRISPR gene editing system, with a DNA sequence selected from sequences as shown in SEQ ID NOs: 1-6 as a target site. A method for preparing porcine fibroblasts and gene-edited pigs, in which both CD163 gene and CD13 gene are knocked-out is established based on the gene knockout vector system. The above vector system and method have the advantages of reducing the difficulty of gene manipulation, improving the knockout efficiency, and rapidly knocking out CD163 gene and CD13 gene. And porcine fibroblasts or gene-edited pigs with CD163 gene and CD13 gene being knocked-out prepared by the above vector and method, in which both CD163 gene and CD13 gene are knocked-out and no exogenous markers are introduced, can provide a research platform for porcine blue ear disease and porcine epidemic diarrhea, and has a very high breeding value.

Porcine embryonic fibroblasts (PEF) in the following examples are prepared as follows: collecting 35-day-old embryos of Large White pigs, removing the fetal head, tail, limbs, internal organs and bones, and cleaning blood off. Curved-tipped ophthalmic scissors are used to continuously and completely shearing the fetus for 30 minutes. The sheared fetal tissue was pipetted into a 15 mL centrifuge tube with an end-cut blue pipette tip, and 5 mL of complete medium was added. Following natural sedimentation for several minutes, the upper solution was removed. To the lower tissue block, a few drops of fetal bovine serum are added. The resulting mixture is sucked with 15 cm glass Pasteur pipette curved at a position 1 cm away from its tip, and plated in two T75 flasks, standing with its bottom being upward. 15 mL of complete medium on the opposite side. The flasks are carefully inverted 6-8 h later to immersing the tissue blocks in the culture solution, followed by changing the medium every two days. After the cells were overgrown with the T75 flasks, they were stored by cryopreservation. The Large White pigs are pigs raised by the pig farm of Institute of Animal Science (IAS) of Chinese Academy of Agricultural Sciences (CAAS).

EXAMPLES

Example 1. Construction of CRISPR/Cas9 Targeting Vector Targeting CD163 Gene and CD13 Gene 1. First, exons of a gene encoding porcine CD163 and exons of CD13 gene were selected as targeting region, and multiple gRNAs targeting CD163 and CD13, i.e., targeting sites, were designed by software. Among them, the targeting sites for CD163 comprise CD163-gRNA1: ggaaacccaggctggttgga (SEQ ID NO: 1); CD163-gRNA2: ggaggggacattccctgctc (SEQ ID NO: 2) and CD163-gRNA3: ggtcgtgttgaagtacaaca (SEQ ID NO: 3). Targeting sites for CD13 comprise: CD13-gRNA1: gcatcctcctcggcgtgg (SEQ ID NO: 4); CD13-gRNA2: caagggattctacatttcca (SEQ ID NO: 5) and CD13-gRNA3: ttctacatttccaaggccct (SEQ ID NO: 6).

2. Complementory paired oligonucleotides were synthesized according to the gRNA sequences described above, as shown in the table below, wherein the lower case letters are the enzyme digestion sites.

TABLE 1

Complementary oligonucleotides for the gRNA sequences

| Name | Sequence 5'-3' |
|---|---|
| CD163-gRNA-F-1 (SEQ ID NO: 7) | caccGGAAACCCAGGCTGGTTGGA |
| CD163-gRNA-R-1 (SEQ ID NO: 8) | aaacTCCAACCAGCCTGGGTTTCC |
| CD163-gRNA-F-2 (SEQ ID NO: 9) | caccGGAGGGGACATTCCCTGCTC |
| CD163-gRNA-R-2 (SEQ ID NO: 10) | aaacGAGCAGGGAATGTCCCCTCC |
| CD163-gRNA-F-3 (SEQ ID NO: 11) | caccGGTCGTGTTGAAGTACAACA |
| CD163-gRNA-R-3 (SEQ ID NO: 12) | aaacTGTTGTACTTCAACACGACC |
| CD13-gRNA-F-1 (SEQ ID NO: 13) | caccGCATCCTCCTCGGCGTGG |
| CD13-gRNA-R-1 (SEQ ID NO: 14) | aaacCCACGCCGAGGAGGATGC |
| CD13-gRNA-F-2 (SEQ ID NO: 15) | caccCAAGGGATTCTACATTTCCA |
| CD13-gRNA-R-2 (SEQ ID NO: 16) | aaacTGGAAATGTAGAATCCCTTG |
| CD13-gRNA-F-3 (SEQ ID NO: 17) | caccTTCTACATTTCCAAGGCCCT |
| CD13-gRNA-R-3 (SEQ ID NO: 18) | aaacAGGGCCTTGGAAATGTAGAA |

3. Construction of CRISPR/Cas9 targeting vector targeting CD163 gene and CD13 gene. The pX330 vector backbone is shown in FIG. 1. The detailed construction method is as follows.

(1) The 6 pairs of synthesized oligonucleotides in Table 1 were treated at 98° C. for 10 min, and then naturally cooled to room temperature and then annealed.

(2) The pX330 backbone vector containing the Cas9 sequence was digested with restriction endonuclease Bbs I at 37° C. for 2 h, and the linearized fragment was recovered by gel cutting.

(3) Thereafter, the linearized fragment was ligated to the annealed oligonucleotide at 16° C. for 1 h, and then transformed into Top10 or DH5α competent cells, and plated on an LB plate containing ampicillin.

(4) A single colony was picked, expanded and sequenced. The sequencing primer was U6-FWD. If the sequence is correct, the expansion is carried out.

(5) The plasmid was extracted by a method using EndoFree Plasmid Maxi Kit, and the extracted plasmid was used for transfection of cells.

Example 2. Establishment of a Large White Pig Fetal Fibroblast Cell Line with Both CD163 Gene and CD13 Gene being Knocked-Out 1. Cell Transfection The primary Large White pig fetal fibroblasts were resuscitated on 6 cm culture dish on the day before transfection, and cell transfection was performed when the cells had a confluence of 70-80%. The transfection step was performed in strict accordance with the instructions of the Basic Primary Fibroblasts Nucleofector Kit (Lonza).

2. Determination of Targeting Efficiency

After electroporation, the cells were cultured for 48 hours, and some cells was used for plating, and some cells were collected for extraction of cell genome, followed by PCR amplification, so as to determine the targeting efficiency. The results showed that the targeting efficiencies of the three gRNAs for CD163 gene were 9%, 5% and 4%, respectively; and the targeting efficiencies of the three gRNAs for CD13 gene were 17%, 12% and 7%, respectively. The two most efficient gRNAs were selected for subsequent experiments, and the two vectors were named pX330-CD163 and pX330-CD13, respectively.

Using the extracted cell genome as a template, PCR was carried out using Pre mix Taq DNA polymerase, and primers for the PCR amplification were as follows.

The primers for the CD163 gene were CD163-F: 5'-aagcc-cactgtaggcagaa-3' (SEQ ID NO: 19) and CD163-R: 5'-ccccaggagggaaaccac-3' (SEQ ID NO: 20). The amplification conditions were as follows: 95° C., 5 min; 95° C., 30 s; 61° C., 30 s; 72° C., 30 s; 72° C., 10 min; 36 cycles, followed by 2% agarose gel electrophoresis for observing bands.

The amplification primers for CD13 gene were CD13-F: 5' tacccagttcagtgaccttcgtc 3' (SEQ ID NO: 21) and CD13-R: 5' tgctcggcattcttgttcttct 3' (SEQ ID NO: 22). The amplification conditions were as follows: 95° C., 5 min; 95° C., 30 s; 58° C., 30 s; 72° C., 30 s; 72° C., 10 min; 34 cycles, followed by 2% agarose gel electrophoresis for observing bands.

3. Screening of Positive Monoclonal Cell Lines

After 48 hours of electroporation, when the cell confluence was about 90%, the cells were plated at a suitable density, and the culture solution was changed every 3 days. The plated cells were cultured for about 10 days, and formation of clones with appropriate size was observed. The monoclonal cells are expanded and a part of the cells are used for extraction of genome to identify the genotype.

4. Identification of Positive Monoclonal Cell Lines

Identification of the selected cell monoclonal comprises performing PCR using Pre mix Taq DNA polymerase using the extracted cell genome as a template.

The amplified fragment of the CD163 gene was 300 bp in length, and the primers were CD163-F: 5' aagcc-cactgtaggcagaa 3' (SEQ ID NO: 19) and CD163-R: 5' ccccaggagggaaaccac 3' (SEQ ID NO: 20). The amplification conditions were as follows: 95° C., 5 min; 95° C., 30 s; 61° C., 30 s; 72° C., 30 s; 72° C., 10 min; 36 cycles.

The target fragment amplified from CD13 gene is 286 bp in length, and the primers were CD13-F: 5' tacccagttcagtgaccttcgtc 3' (SEQ ID NO: 21) and CD13-R: 5' tgctcggcattcttgttcttct 3' (SEQ ID NO: 22). The amplification conditions were as follows: 95° C., 5 min; 95° C., 30 s; 58° C., 30 s; 72° C., 30 s; 72° C., 10 min; 34 cycles.

The bands obtained by 2% agarose gel electrophoresis were observed, and the PCR products were sequenced by Beijing Tianyi Huiyuan Company. According to the sequencing results, the cell lines with double-gene frame-shift mutation were screened and served as donor cells for nuclear transfer.

5. Experimental Results

The sequencing results showed that we successfully obtained a plurality of porcine fetal fibroblast cell lines with both CD163 gene and CD13 gene being knocked-out, and genotypes of some of the double knockout cell lines are shown in FIG. 2.

Example 3. Method for Preparing Gene-Edited Pigs with Both CD163 Gene and CD13 Gene being Knocked-Out by Somatic Cell Nuclear Transfer Technique The positive cells obtained in Example 2 were used as donor cells for nuclear transfer, and the young pig oocytes matured in vitro for 40 hours were used as recipient cells for nuclear transfer. The donor cells for nuclear transfer were transferred into enucleated oocytes, followed by electrofusion and activation, to construct recombinant clonal embryos. The clonal recombinant embryos with good developmental condition were selected to be surgically transferred into the uterus of natural-estrus multiparous sows for pregnancy. The surgical embryo transfer procedure comprises performing anesthesia with ventilator, maintaining anesthesia with 2% chloral hydrate, supine restraining on surgical frame, making a surgical incision about 10 cm long along a midline of the abdomen to expose the ovary, fallopian tube and uterus, allowing embryo-transfer glass tube to enter fallopian tube about 5 cm in depth along fimbria of fallopian tube, and transplanting clonal recombinant embryo with good developmental state to the joint between ampulla and isthmus of fallopian tube. After the embryo transfer, estrus returning situation was observed by the technician, and the recipient sow was examined for pregnancy status regularly using the B-mode ultrasound.

Experimental results showed genetically edited pigs with both CD163 gene and CD13 gene being knocked-out were obtained successfully.

It should be noted that the above embodiments are only used to illustrate the technical solutions of the present disclosure, but not used to limit the present disclosure. Although the present disclosure has been described in detail with reference to various embodiments, those skilled in the art should understand that modifications of the technical solutions described in various embodiments or substitutions to some or all of the technical features can be made, and the modifications or substitutions do not depart from the scope of the technical solutions of the embodiments of the present disclosure.

INDUSTRIAL APPLICABILITY

The present disclosure constructs a vector system for knocking out CD163 gene and CD13 gene, by using a CRISPR gene editing system, with a DNA sequence selected from sequences as shown in SEQ ID NOs: 1-6 as a target site. A method for preparing porcine fibroblasts and gene-edited pigs, in which both CD163 gene and CD13 gene are knocked-out is established based on the gene knockout vector system. The above vector system and method have the advantages of reducing the difficulty of gene manipulation, improving the knockout efficiency, and rapidly knocking out CD163 gene and CD13 gene. And porcine fibroblasts or gene-edited pigs with CD163 gene and CD13 gene being knocked-out prepared by the above vector and method, in which both CD163 gene and CD13 gene are knocked-out and no exogenous markers are introduced, can provide a research platform for porcine blue ear disease and porcine epidemic diarrhea, and has a very high breeding value.

What is claimed is:

1. A double-gene knockout vector system comprising:
   i) a CD163 gene knockout vector comprising:
      a) a nucleic acid sequence encoding Cas9, and
      b) a pair of guide RNAs (gRNAs) that target SEQ ID NO: 1, 2, or 3 of the *Sus scrofa* pig CD163 gene; and
   ii) a CD13 gene knockout vector comprising:
      a) a nucleic acid sequence encoding Cas9, and
      b) a pair of guide RNAs (gRNAs) that target SEQ ID NO: 4, 5, or 6 of the *Sus scrofa* pig CD13 gene.

2. The vector system according to claim 1, wherein the pair of guide RNAs (gRNAs) in the CD163 gene knockout vector comprise the nucleic acid sequences of SEQ ID NO: 7 and 8.

3. The vector system according to claim 1, wherein the pair of guide RNAs (gRNAs) in the CD13 gene knockout vector comprise the nucleic acid sequences of SEQ ID NO: 13 and 14.

4. A method for preparing *Sus scorfa* pig fibroblasts with homozygous knock outs of both the CD163 gene and CD13 gene, the method comprising:
   (a) transfecting isolated *Sus scorfa* pig fibroblasts with the knockout vector system of claim 1;
   (b) screening the *Sus scrofa* pig fibroblasts obtained in step a) for *Sus scrofa* pig fibroblasts with homozygous knockouts of the CD163 and CD13 genes,
   such that *Sus scrofa* pig fibroblasts with homozygous knockouts of both the CD163 and CD13 genes are obtained.

5. The method according to claim 4, wherein the isolated *Sus scorfa* pig fibroblasts are fetal fibroblasts.

6. The method according to claim 4, wherein in the transfection is is achieved by electroporation.

7. A method of preparing a *Sus scrofa* pig that is resistant to porcine epidemic diarrhea virus (PEDV) and porcine reproductive and respiratory syndrome virus (PRRSV) infection, the method comprising:
   i) transferring the cell nucleus of a *Sus scrofa* pig fibroblast with homozygous knockouts of both the CD163 and CD13 genes obtained by the method of claim 4 into an enucleated *Sus scrofa* pig oocyte;
   ii) fusing the nucleus and oocyte such that a recombinant cloned embryo is obtained;
   iii) transplanting the recombinant cloned embryo obtained in step a) into a recipient female such that a *Sus scrofa* pig with homozygous knockouts of both the CD163 and CD13 genes and resistance to PEDV and PRRSV infection is obtained.

8. The method according to claim 7, further comprising screening the pig obtained in step iii) by:
   a) extracting genomic DNA from the pig obtained in step iii);
   b) amplifying the genomic DNA using a primer pair that is the nucleic acid sequences of SEQ ID NO: 19 and 20 or SEQ ID NO: 21 and 22;
   c) electrophoresing or sequencing the amplified DNA obtained in step b), and
   d) determining whether the CD163 gene and CD13 genes have been knocked out using information collected from the electrophoresing or sequencing in step c).

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: CD163-gRNA1

<400> SEQUENCE: 1
ggaaacccag gctggttgga                                                 20

<210> SEQ ID NO 2
<211> LENGTH: 20
<212> TYPE: DNA
<213> ORGANISM: Artificial Sequence
<220> FEATURE:
<223> OTHER INFORMATION: CD163-gRNA2

<400> SEQUENCE: 2
ggaggggaca ttccctgctc                                                 20

<210> SEQ ID NO 3
<211> LENGTH: 20
<212> TYPE: DNA
<213> ORGANISM: Artificial Sequence
<220> FEATURE:
<223> OTHER INFORMATION: CD163-gRNA3

<400> SEQUENCE: 3
ggtcgtgttg aagtacaaca                                                 20

<210> SEQ ID NO 4
<211> LENGTH: 18
<212> TYPE: DNA
<213> ORGANISM: Artificial Sequence
<220> FEATURE:
<223> OTHER INFORMATION: CD13-gRNA1

<400> SEQUENCE: 4
gcatcctcct cggcgtgg                                                   18

<210> SEQ ID NO 5
<211> LENGTH: 20
<212> TYPE: DNA
<213> ORGANISM: Artificial Sequence
<220> FEATURE:
<223> OTHER INFORMATION: CD13-gRNA2

<400> SEQUENCE: 5
caagggattc tacatttcca                                                 20

<210> SEQ ID NO 6
<211> LENGTH: 20
<212> TYPE: DNA
<213> ORGANISM: Artificial Sequence
<220> FEATURE:
<223> OTHER INFORMATION: CD13-gRNA3

<400> SEQUENCE: 6
ttctacattt ccaaggccct                                                 20

<210> SEQ ID NO 7
<211> LENGTH: 24
<212> TYPE: DNA
<213> ORGANISM: Artificial Sequence

```
<220> FEATURE:
<223> OTHER INFORMATION: CD163-gRNA-F-1

<400> SEQUENCE: 7
caccggaaac ccaggctggt tgga                                              24

<210> SEQ ID NO 8
<211> LENGTH: 24
<212> TYPE: DNA
<213> ORGANISM: Artificial Sequence
<220> FEATURE:
<223> OTHER INFORMATION: CD163-gRNA-R-1

<400> SEQUENCE: 8
aaactccaac cagcctgggt ttcc                                              24

<210> SEQ ID NO 9
<211> LENGTH: 24
<212> TYPE: DNA
<213> ORGANISM: Artificial Sequence
<220> FEATURE:
<223> OTHER INFORMATION: CD163-gRNA-F-2

<400> SEQUENCE: 9
caccggaggg gacattccct gctc                                              24

<210> SEQ ID NO 10
<211> LENGTH: 24
<212> TYPE: DNA
<213> ORGANISM: Artificial Sequence
<220> FEATURE:
<223> OTHER INFORMATION: CD163-gRNA-R-2

<400> SEQUENCE: 10
aaacgagcag ggaatgtccc ctcc                                              24

<210> SEQ ID NO 11
<211> LENGTH: 24
<212> TYPE: DNA
<213> ORGANISM: Artificial Sequence
<220> FEATURE:
<223> OTHER INFORMATION: CD163-gRNA-F-3

<400> SEQUENCE: 11
caccggtcgt gttgaagtac aaca                                              24

<210> SEQ ID NO 12
<211> LENGTH: 24
<212> TYPE: DNA
<213> ORGANISM: Artificial Sequence
<220> FEATURE:
<223> OTHER INFORMATION: CD163-gRNA-R-3

<400> SEQUENCE: 12
aaactgttgt acttcaacac gacc                                              24

<210> SEQ ID NO 13
<211> LENGTH: 22
<212> TYPE: DNA
<213> ORGANISM: Artificial Sequence
<220> FEATURE:
<223> OTHER INFORMATION: CD13-gRNA-F-1

<400> SEQUENCE: 13
caccgcatcc tcctcggcgt gg                                                22
```

-continued

```
<210> SEQ ID NO 14
<211> LENGTH: 22
<212> TYPE: DNA
<213> ORGANISM: Artificial Sequence
<220> FEATURE:
<223> OTHER INFORMATION: CD13-gRNA-R-1

<400> SEQUENCE: 14
aaacccacgc cgaggaggat gc                                                 22

<210> SEQ ID NO 15
<211> LENGTH: 24
<212> TYPE: DNA
<213> ORGANISM: Artificial Sequence
<220> FEATURE:
<223> OTHER INFORMATION: CD13-gRNA-F-2

<400> SEQUENCE: 15
cacccaaggg attctacatt tcca                                               24

<210> SEQ ID NO 16
<211> LENGTH: 24
<212> TYPE: DNA
<213> ORGANISM: Artificial Sequence
<220> FEATURE:
<223> OTHER INFORMATION: CD13-gRNA-R-2

<400> SEQUENCE: 16
aaactggaaa tgtagaatcc cttg                                               24

<210> SEQ ID NO 17
<211> LENGTH: 24
<212> TYPE: DNA
<213> ORGANISM: Artificial Sequence
<220> FEATURE:
<223> OTHER INFORMATION: CD13-gRNA-F-3

<400> SEQUENCE: 17
caccttctac atttccaagg ccct                                               24

<210> SEQ ID NO 18
<211> LENGTH: 24
<212> TYPE: DNA
<213> ORGANISM: Artificial Sequence
<220> FEATURE:
<223> OTHER INFORMATION: CD13-gRNA-R-3

<400> SEQUENCE: 18
aaacagggcc ttggaaatgt agaa                                               24

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
aagcccactg taggcagaa                                                     19

<210> SEQ ID NO 20
<211> LENGTH: 18
<212> TYPE: DNA
<213> ORGANISM: Artificial Sequence
<220> FEATURE:
<223> OTHER INFORMATION: primer
```

```
<400> SEQUENCE: 20
ccccaggagg gaaaccac                                                   18

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tacccagttc agtgaccttc gtc                                             23

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
tgctcggcat tcttgttctt ct                                              22
```